(12) United States Patent
Gantos et al.

(10) Patent No.: US 10,981,023 B2
(45) Date of Patent: Apr. 20, 2021

(54) VENT MONITORING SYSTEM

(71) Applicant: CARDINAL IP HOLDING, LLC, Milwaukee, WI (US)

(72) Inventors: Jill L. Gantos, Nunica, MI (US); Peter M. Schmitz, Byron Center, MI (US)

(73) Assignee: Cardinal IP Holding, LLC, Milwaukee, WI (US)

( * ) Notice: Subject to any disclaimer, the term of this patent is extended or adjusted under 35 U.S.C. 154(b) by 0 days.

(21) Appl. No.: 16/129,539

(22) Filed: Sep. 12, 2018

(65) Prior Publication Data

US 2019/0351267 A1 Nov. 21, 2019

Related U.S. Application Data

(60) Provisional application No. 62/672,954, filed on May 17, 2018.

(51) Int. Cl.
*G08B 21/12* (2006.01)
*A62C 3/04* (2006.01)
(Continued)

(52) U.S. Cl.
CPC .................. *A62C 3/04* (2013.01); *F23J 99/00* (2013.01); *G01K 1/02* (2013.01); *G01N 21/55* (2013.01);
(Continued)

(58) Field of Classification Search
CPC ........... A61B 6/4258; B22C 9/04; B22C 9/10; B23P 15/246; B29C 33/301; B29C 33/38; B29C 33/3835; C08L 63/00; C08L 83/04; Y10T 428/24479; B01D 2251/104; B01D 2256/10; B01D 2256/12; B01D 53/22; B01D 53/261; B01D 53/9431; B03B 9/06; C01B 13/10; C01B 13/11; C01B 2201/64; C10J 2200/09; C10J 2200/156; C10J 2300/0903; C10J 2300/0956; C10J 2300/0973; C10J 2300/1606; C10J 2300/1646; C10J 2300/165;
(Continued)

(56) References Cited

U.S. PATENT DOCUMENTS 4,910,501 A 3/1990 Montoya
6,220,229 B1 * 4/2001 Kawamura ........ F02M 25/0809
123/520

(Continued)

FOREIGN PATENT DOCUMENTS

EP 2366950 A1 * 9/2011 ............... F23J 13/00
EP 2366950 A1 9/2011
WO 2015104021 A1 7/2015

*Primary Examiner* — Daniel Previl
(74) *Attorney, Agent, or Firm* — Warner Norcross + Judd LLP

(57) ABSTRACT

Embodiments of the present disclosure are directed to a vent monitoring system that includes a first sensor configured to provide feedback indicative of an amount of a substance accumulated in the vent, a second sensor configured to provide feedback indicative of a temperature in the vent, and a control system communicatively coupled to the first sensor and the second sensor, where the control system is configured to generate a notification when the feedback from the first sensor exceeds a first target level and when the feedback from the second sensor exceeds a second target level.

24 Claims, 4 Drawing Sheets

(51) Int. Cl.
*F23J 99/00* (2006.01)
*G01K 1/02* (2021.01)
*G01N 33/00* (2006.01)
*G08B 21/18* (2006.01)
*G01N 21/55* (2014.01)

(52) U.S. Cl.
CPC ......... *G01N 33/004* (2013.01); *G08B 21/182* (2013.01); *F23J 2213/70* (2013.01); *G01N 2021/555* (2013.01)

(58) Field of Classification Search
CPC .................. C10J 2300/1671; C10J 2300/169; C10J 3/16; C10J 3/24; C10J 3/721; C10J 3/723; C25B 1/13; F01N 2240/38; F01N 2610/02; F01N 2610/06; F01N 2610/08; F01N 2610/11; F01N 3/2066; F23G 2201/10; F23G 2201/40; F23G 2201/601; F23G 2201/602; F23G 2201/603; F23G 2201/702; F23G 2206/203; F23G 2207/101; F23G 2207/102; F23G 2900/50209; F23G 5/006; F23G 5/02; F23G 5/027; F23G 5/033; F23G 5/05; F23G 5/12; F23G 5/24; F23G 5/46; F23G 5/50; F23J 15/025; F23L 2900/07005; F23L 2900/07009; F23L 7/00; Y02E 20/12; Y02E 20/344; Y02E 50/10; Y02E 50/30; Y02P 20/129; Y02T 10/24; Y02W 30/523; Y02W 30/622; A23C 9/1425; A23C 9/1427; A23C 9/144; A23K 40/00; A23L 27/40; A23L 27/84; A23N 17/00; A23V 2002/00; B01F 15/00233; B01F 15/00253; B01F 15/00396; B01F 15/0203; B01F 15/0445; B01F 15/065; B01F 5/10; B01F 7/021; C12G 1/0216; D06F 2058/2838; D06F 2058/2896; D06F 58/28; D21G 9/0009; F01D 25/16; F01D 25/22; F04D 29/056; F05D 2240/51; F05D 2240/53; F05D 2240/54; F16C 32/0402; F16C 32/0423; F16C 32/0442; F16C 32/0607; F16C 32/0614; F16C 32/0625; F16C 32/0677; F16C 32/0681; F16C 32/0685; F16C 32/0696; G01N 1/22; G01N 1/38; G01N 2001/381; G01N 27/404; G05D 22/02; Y10S 426/807
USPC ...... 340/540, 516, 506–507, 538.15, 539.22, 340/545.3–545.6, 555–556, 632, 641, 340/691.6
See application file for complete search history.

(56) References Cited

U.S. PATENT DOCUMENTS

| | | | | |
|---|---|---|---|---|
| 6,460,579 | B2* | 10/2002 | Nanaji | ................. B67D 7/0486 |
| | | | | 141/59 |
| 10,460,586 | B1* | 10/2019 | Walma | ...................... G08B 7/06 |
| 2007/0059986 | A1* | 3/2007 | Rockwell | ........... G01R 19/2513 |
| | | | | 439/638 |
| 2008/0282606 | A1* | 11/2008 | Plaza | ...................... C10L 1/026 |
| | | | | 44/308 |
| 2009/0144015 | A1 | 6/2009 | Bedard | |
| 2013/0076351 | A1* | 3/2013 | Moon | ................ G01R 33/0023 |
| | | | | 324/251 |
| 2014/0043167 | A1* | 2/2014 | Michailoff | .............. F24B 1/187 |
| | | | | 340/584 |
| 2014/0069474 | A1* | 3/2014 | Forde | ...................... A62C 3/04 |
| | | | | 134/56 R |
| 2015/0377677 | A1* | 12/2015 | Tenhunen | ............... G01S 17/88 |
| | | | | 356/5.01 |

* cited by examiner

VENT MONITORING SYSTEM

CROSS REFERENCE TO RELATED APPLICATIONS

This application claims priority from and the benefit of U.S. Provisional Application Ser. No. 62/672,954, entitled "VENT MONITORING SYSTEM," filed May 17, 2018, which is hereby incorporated by reference in its entirety for all purposes.

BACKGROUND

The present disclosure relates generally to monitoring systems, and more particularly, to a vent or chimney monitoring system.

Vents may be utilized to direct various gases, such as smoke, steam, air, other exhaust gases, from within a structure or enclosure toward an external or ambient environment. In some cases, liquid or solid materials may be captured or otherwise mixed with the gases being directed toward the external or ambient environment through the vent. Such materials may ultimately accumulate within a conduit of the vent, which could limit or restrict a flow of the gases through the vent. In addition to limiting the flow of the gases through the vent, the accumulation of the liquid or solid materials may reduce an efficiency of a system utilizing the vent, such as a fireplace, a boiler, a burner, or a dryer. Existing monitoring systems for vents typically rely on feedback indicative of a temperature within the vent to determine a condition of the vent. Unfortunately, the temperature within the vent may not provide a comprehensive analysis of the condition of the vent and may not enable maintenance of the vent to be performed before a potential risk event occurs.

DRAWINGS

SUMMARY

Figure 1:
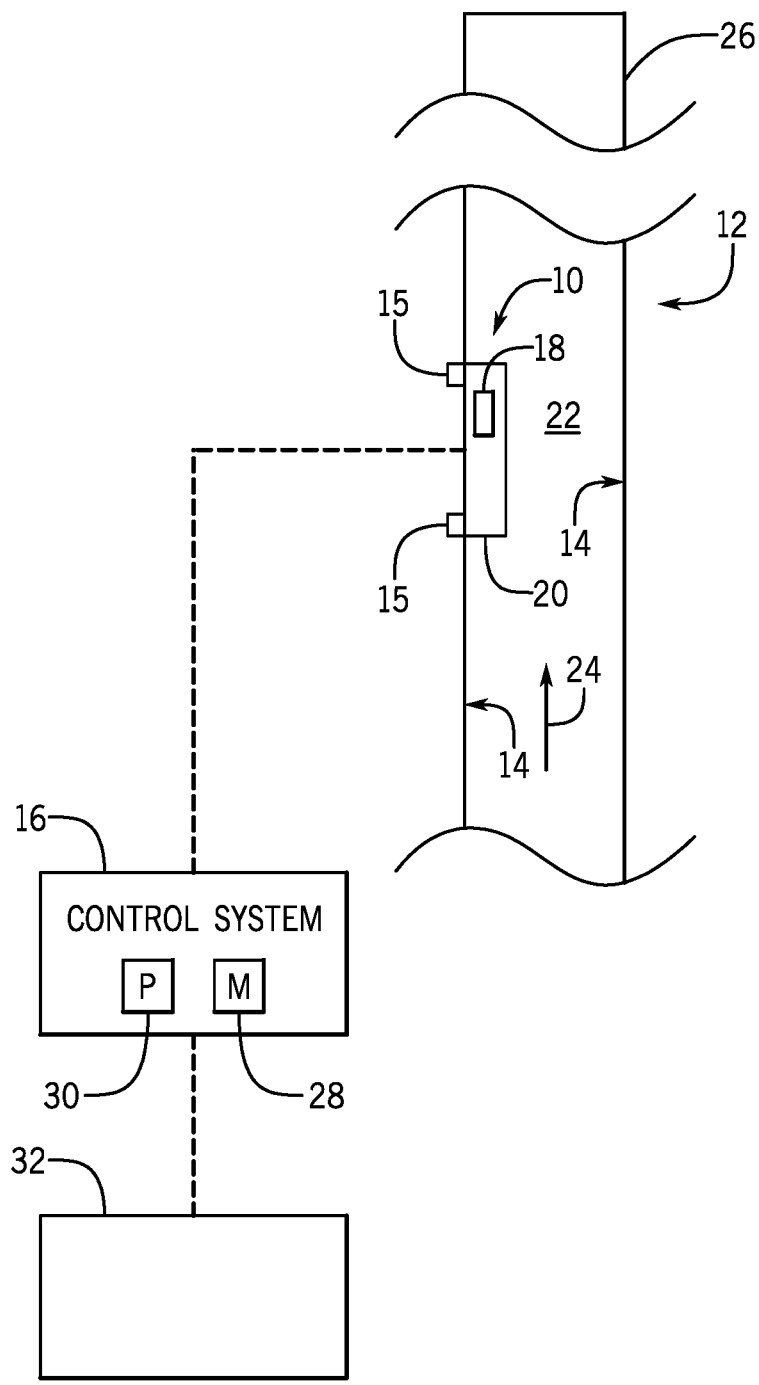
FIG. 1 is a schematic of an embodiment of a vent monitoring system disposed within a vent, in accordance with an aspect of the present disclosure.

In one embodiment of the present disclosure, a monitoring system for a vent includes a first sensor configured to provide feedback indicative of an amount of a substance accumulated in the vent, a second sensor configured to provide feedback indicative of a temperature in the vent, and a control system communicatively coupled to the first sensor and the second sensor, where the control system is configured to generate a notification when the feedback from the first sensor exceeds a first target level and when the feedback from the second sensor exceeds a second target level.

In another embodiment of the present disclosure, a monitoring system includes a housing configured to be mounted to an interior surface of a vent, a first sensor disposed at least partially within the housing, where the first sensor is configured to provide feedback indicative of an amount of a substance accumulated in the vent, a second sensor disposed at least partially within the housing, where the second sensor is configured to provide feedback indicative of a temperature in the vent, and a control system disposed within the housing, where the control system is communicatively coupled to the first sensor and the second sensor, and the control system is configured to generate a notification to perform maintenance on the vent when the feedback from the first sensor reaches a first target level, when the feedback from the second sensor reaches a second target level, or both.

In a further embodiment of the present disclosure, a tangible, non-transitory, machine-readable medium, includes instructions that, when executed by a processor, cause the processor to receive feedback from a first sensor of a vent monitoring system, where the feedback from the first sensor is indicative of an amount of a substance accumulated in a vent, receive feedback from a second sensor of the vent monitoring system, where the feedback from the second sensor is indicative of a temperature within the vent, compare the feedback from the first sensor to a first threshold value and compare the feedback from the second sensor to a second threshold value, and output a notification in response to the feedback from the first sensor exceeding the first threshold value, the feedback from the second sensor exceeding the second threshold value, or both.

Other features and advantages of the present application will be apparent from the following, more detailed description of the embodiments, taken in conjunction with the accompanying drawings which illustrate, by way of example, the principles of the application.

DETAILED DESCRIPTION

The present disclosure is directed to an enhanced or improved vent monitoring system. Existing vent monitoring systems primarily utilize temperature sensors to determine a condition of a vent and/or within a conduit of the vent. Unfortunately, a temperature within the vent may not be indicative of potential conditions within the vent that are of interest. Additionally, existing systems that monitor parameters in addition to temperature may be utilized to detect that combustion is occurring in order to activate a fire suppression device. As such, the existing systems may generate an output after a risk event, such as combustion, has already occurred.

Embodiments of the present disclosure are directed to a system that is configured to monitor a condition of the vent using a plurality of sensors. The system may utilize feedback from each of the plurality of sensors to determine that the vent should incur maintenance, such as cleaning, accumulation removal, structural integrity repairs, or any other suitable maintenance. In some embodiments, the system may be communicatively coupled to an external electronic device that is configured to provide maintenance notifications to a user or directly to a maintenance service provider. For example, the external electronic device may include a smart phone, a mobile device, a tablet, a smart wearable device, a laptop computer, a desktop computer, or any other suitable electronic device that may provide notifications to a user. Additionally, the plurality of sensors may be included in a single-packaged unit configured to facilitate streamlined installation of the system into an existing vent or a recently manufactured vent. The single-packaged unit may enable each sensor of the plurality of sensors to be installed in the vent by simply coupling the single-packaged unit to a predetermined location in the vent or vent conduit.

The plurality of sensors may include a temperature sensor, an accumulation sensor, a concentration sensor, a flow sensor, another suitable sensor, or any combination thereof. In some embodiments, the temperature sensor includes a thermocouple, a thermometer, a resistance-based temperature sensor, or another suitable device configured to provide feedback indicative of a temperature in the vent or vent conduit. The accumulation sensor may include a photoelectric sensor, a resistance-based accumulation sensor, a capacitance-based accumulation sensor, or another suitable device configured to provide feedback indicative of accumulation of a substance, such as creosote, ash, dust, lent, grease, or another substance that may be present in the vent or vent conduit. The concentration sensor may include a device configured to determine a concentration of various gases within the vent, such as carbon monoxide, carbon dioxide, water, or another gas. The flow rate sensor may include a venture, an orifice, a pitot tube, a nozzle, a rotameter, a Coriolis sensor, an ultrasonic sensor, or any other suitable device configured to provide feedback indicative of a flow rate of a substance through the vent or vent conduit.

Turning now to the drawings, FIG. 1 illustrates a schematic of an embodiment of a vent monitoring system 10. As shown in the illustrated embodiment of FIG. 1, the vent monitoring system 10 is disposed within a vent 12 and may be mounted on an interior surface 14 of the vent 12. In some embodiments, the vent monitoring system 10 is mounted to the interior surface 14 of the vent 12 via a mount 15. The mount 15 may include a fastener, such as screws, bolts, and/or rivets, a bracket, an adhesive, a weld, a stand, another suitable technique, or any combination thereof. In any case, the mount 15 may position the vent monitoring system 10 at a location within the vent 12 that may incur significant wear and/or may be susceptible to accumulation of solids or liquids that are included in, or mixed with, a fluid flowing through the vent 12.

The vent monitoring system 10 may provide feedback indicative of a condition of the vent 12 to a control system 16. As mentioned above, the vent monitoring system 10 includes a plurality of sensing devices 18 disposed within a housing 20. The plurality of sensing devices 18 may include various devices, such as sensors, that are configured to provide feedback indicative of conditions within an interior portion 22 of the vent 12. In some embodiments, the interior portion 22 of the vent 12 is configured to receive, and/or otherwise direct, a fluid along a flow path 24 toward an exhaust 26. As such, the vent 12 may direct the fluid along the flow path 24 from an interior of a structure toward the exhaust 26.

In some embodiments, the vent 12 includes a chimney, a boiler vent, a cooking vent, a bathroom vent, a vent of a heating and/or cooling system, a dryer vent, and/or another conduit configured to exhaust a fluid to a particular location, such as an ambient environment surrounding a structure associated with the vent 12. As used herein, the fluid may include a mixture of gases, liquids, and/or solids. For example, the gases within the fluid may include smoke, carbon dioxide, carbon monoxide, oxygen, hydrocarbons, refrigerants, nitrogen, air, another suitable gas, or any combination thereof. Additionally, the liquids present in the fluid may include water, grease, non-combusted liquid fuel, liquid refrigerants, another suitable liquid, or any combination thereof. Further, the solids in the fluid may include ash, dust, lent, creosote, food particulates, or other suitable solid particles.

Due to the variety of substances that may be present in the fluid directed through the vent 12, it is now recognized that including the plurality of sensing devices 18 in the vent monitoring system 10 enables the vent monitoring system 10 to generate a comprehensive evaluation of conditions within the vent 12. As such, the plurality of sensing devices 18 may be communicatively coupled to the control system 16, such that the control system 16 may utilize feedback from the plurality of sensing devices 18 to determine various conditions within the vent 12. For instance, the control system 16 may determine an amount of accumulation of a substance within the vent 12, a temperature within the vent 12, a concentration of a particular substance within the fluid flowing through the vent 12, a flow rate of the fluid flowing through the vent 12, or another suitable condition.

The control system 16 may include a memory 28 and a processor 30. The memory 28 may be a mass storage device, a flash memory device, removable memory, or any other non-transitory computer-readable medium that contains instructions regarding control of the vent monitoring system 10. The memory 28 may also include volatile memory such as randomly accessible memory (RAM) and/or non-volatile memory such as hard disc memory, flash memory, and/or other suitable memory formats. The processor 30 may execute the instructions stored in the memory 28, such as instructions for analyzing feedback received from the plurality of sensing devices 18 to determine a condition of the vent 12.

Upon determining a condition of the vent 12, the control system 16 may be configured to generate a signal to an external electronic device 32, which may notify a user or a serviceperson about the condition of the vent 12. The external electronic device 32 may include a smart phone, a mobile device, a tablet, a smart wearable device, a laptop computer, a desktop computer, an alarm system, a display, or any other suitable electronic device that may provide notifications to a user. For instance, the control system 16 may be wirelessly coupled to the electronic device 32 via Wi-Fi, Bluetooth, Zigbee, and/or another suitable wireless communication protocol. In other embodiments, the control system 16 may be coupled to the electronic device 32 through a wired connection or cabled connection. When the control system 16 determines that service should be performed to the vent 12 based on the feedback from the plurality of sensing devices 18, the control system 16 may send an alert or other notification to the electronic device 32 to notify the user or serviceperson. For example, the alert or other notification may include a text message, a phone call, an e-mail, a push notification, an audible sound or alert, a visual cue or alert, a haptic cue or alert, or any combination thereof. In some embodiments, the external electronic device 32 may include multiple electronic devices, such that the user and/or the serviceperson are directed to perform maintenance on the vent 12 through multiple notifications.

Figure 2:
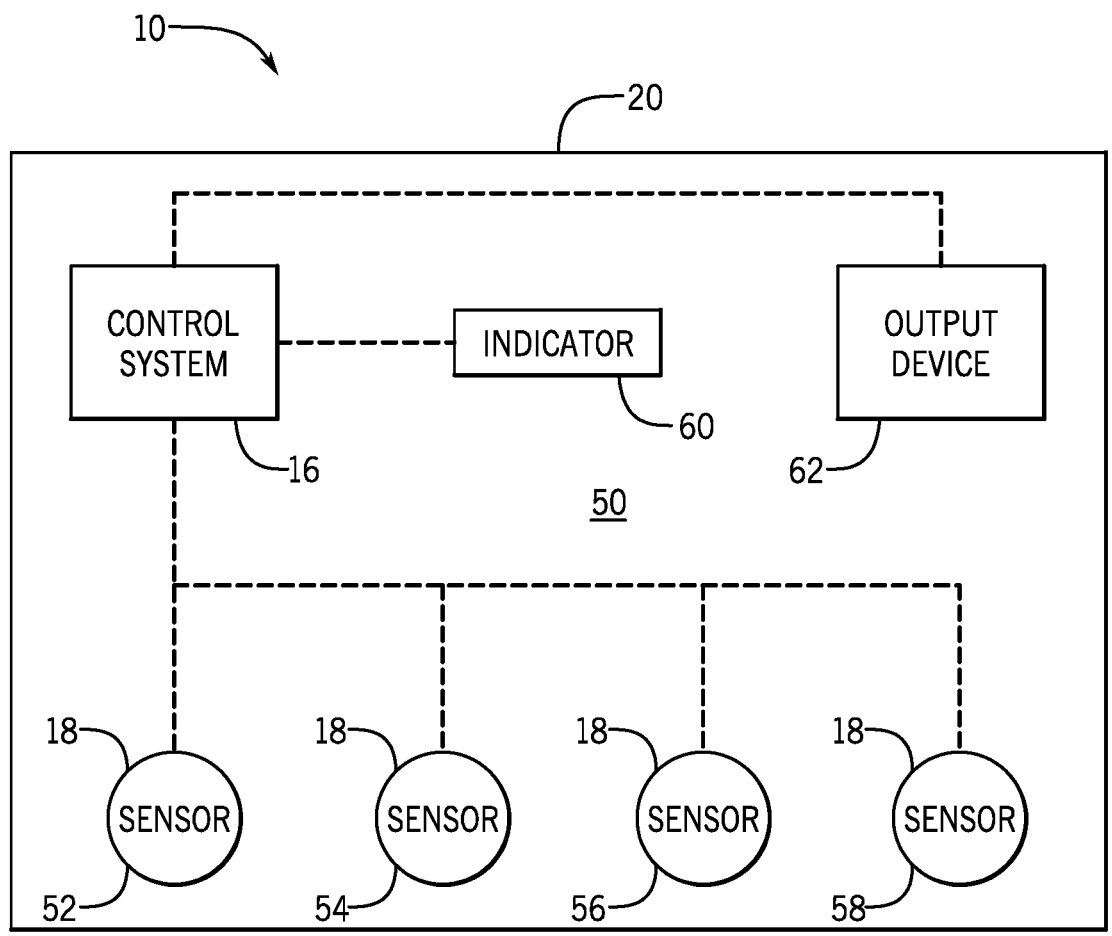
FIG. 2 is a schematic of an embodiment of the vent monitoring system of FIG. 1 as a single-packaged unit, in accordance with an aspect of the present disclosure.

While the illustrated embodiment of FIG. 1 shows the control system 16 external to the vent monitoring system 10, in other embodiments, the control system 16 may be integrated with, or disposed in the housing 20 of, the vent monitoring system 10. For example, FIG. 2 is a schematic of an embodiment of the vent monitoring system 10. The vent monitoring system 10 includes the plurality of sensing devices 18 coupled to the control system 16. In some embodiments, the plurality of sensing devices 18 extend from within an interior 50 of the housing 20 and into the interior portion 22 of the vent 12. As such, the plurality of sensing devices 18 may be configured to be exposed to or contact the fluid flowing through the vent 12 along the flow path 24 to monitor various characteristics of the fluid. Additionally or alternatively, a sensing device of the plurality of sensing devices 18 may be substantially enclosed within the interior 50 of the housing 20. In such cases, the sensing device of the plurality of sensing devices 18 may monitor characteristics of the interior 22 of the vent 12 without being exposed to the fluid flowing through the vent 12.

As discussed above, the plurality of sensing devices 18 may include a temperature sensor 52, an accumulation sensor 54, a concentration sensor 56, a flow sensor 58, another suitable sensor, or any combination thereof. In some embodiments, the temperature sensor 52 includes a thermocouple, a thermometer, a resistance-based temperature sensor, or another suitable device configured to provide feedback indicative of a temperature in the vent 12. The accumulation sensor 54 may include a photoelectric sensor, a resistance-based accumulation sensor, a capacitance-based accumulation sensor, or another suitable device configured to provide feedback indicative of accumulation of a substance, such as creosote, ash, dust, lent, grease, or another substance that may be present in the vent 12. The concentration sensor 56 may include a device configured to determine a concentration of various gases within the vent, such as carbon monoxide, carbon dioxide, water, or another gas. The flow rate sensor 58 may include a venturi, an orifice, a pitot tube, a nozzle, a rotameter, a Coriolis sensor, an ultrasonic sensor, or any other suitable device configured to provide feedback indicative of a flow rate of a substance through the vent 12. In some embodiments, the temperature sensor 52, the concentration sensor 56, and the flow sensor 58 extend from the interior 50 of the housing 20 into the flow path 24 of the fluid through the vent 12. Additionally, the accumulation sensor 54 may be configured to detect buildup of various substances within the vent 12 without contacting the fluid flowing through the vent 12 and/or the accumulated substance. As discussed in detail below, the accumulation sensor 54 may detect an intensity of light reflected off of the interior surface 14 of the vent 12, or via another suitable technique, without contacting the fluid flowing through the vent 12 and/or the accumulated substance.

Additionally, the vent monitoring system 10 includes an indicator 60, which may be configured to further notify the user or serviceperson that maintenance of the vent 12 may be performed. In some embodiments, the indicator 60 includes a light emitting diode configured to change from a green color when the conditions in the vent 12 indicate that maintenance should not be performed to a red color when the conditions in the vent 12 indicate that maintenance should be conducted. In other embodiments, the indicator 60 may illuminate when conditions in the vent 12 indicate that maintenance should be conducted. As such, the light from the light emitting diode may be illuminate a portion of the vent 12 that is visible to the user or serviceperson. Additionally or alternatively, the indicator 60 may include an audible device, such as a speaker, that is configured to output a sound alerting the user or a serviceperson that maintenance should be performed. The audible device may be configured to emit a sound within the vent 12 that may be heard by the user or serviceperson located external to the vent 12.

Further still, the vent monitoring system 10 may include an output device 62 configured to transmit a signal to the external electronic device 32. The output device 62 may include a transmitter that is configured to communicatively couple to the external electronic device 32 via Wi-Fi, Bluetooth, Zigbee, a cabled or wired connection, or via another suitable technique. The control system 16 may be configured to initiate the transmission of the signal as well as to provide a content of the signal. For instance, in some embodiments, the control system 16 may determine that maintenance should be performed and provide a timeline or schedule for when the maintenance should be conducted. Additionally, the control system 16 may provide a list of tasks to complete a suggested maintenance of the vent 12. The content of the signal transmitted by the output device 62 may be based on the feedback received from the plurality of sensing devices 18 and/or the instructions stored in the memory 28 of the control system 16.

Figure 3:
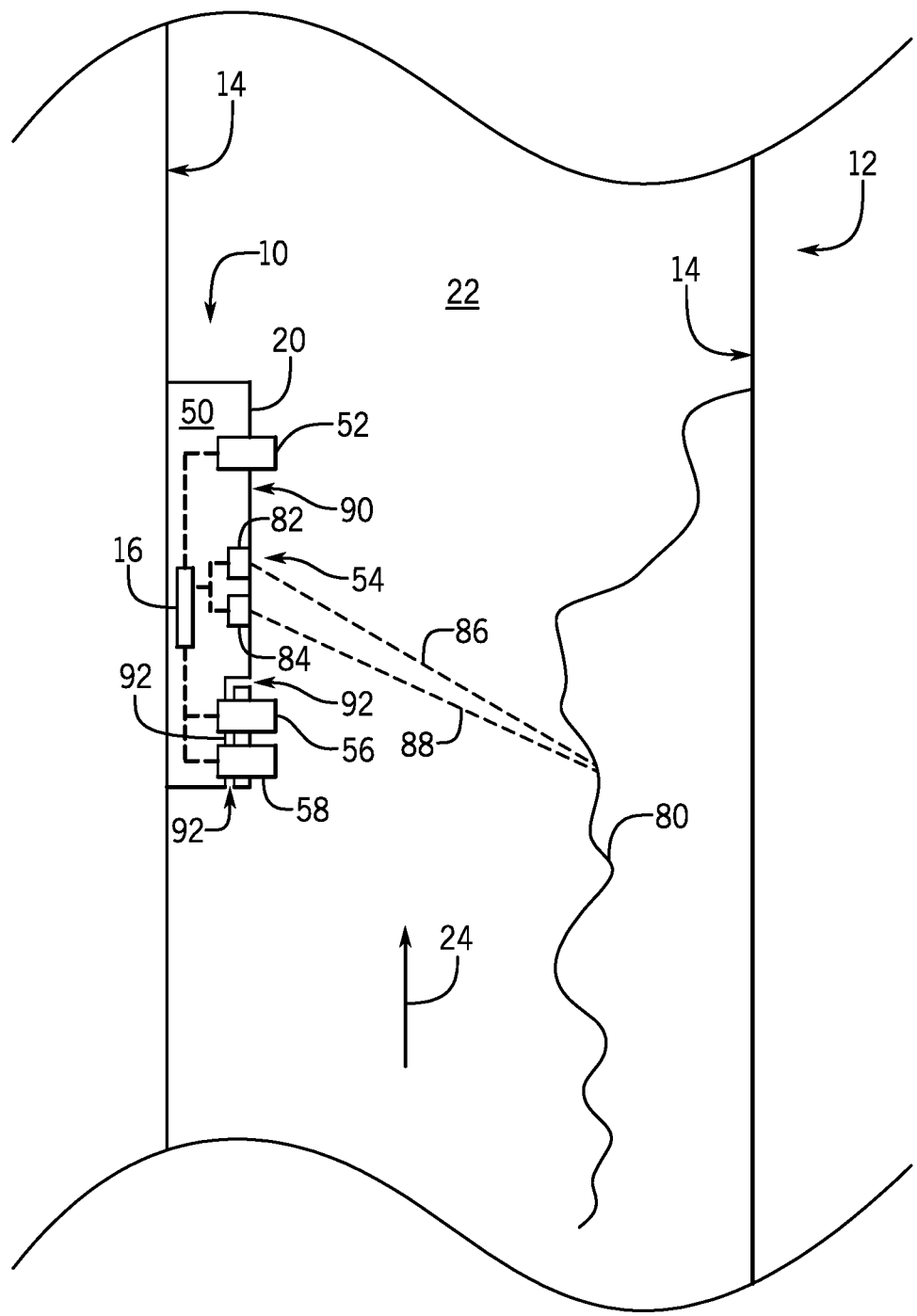
FIG. 3 is a schematic of an embodiment of an accumulation sensor of the vent monitoring system of FIGS. 1 and 2, in accordance with an aspect of the present disclosure.

As discussed above, the vent monitoring system 10 may include the accumulation sensor 54, which may be configured to detect accumulation of a substance, such as creosote, ash, dust, lent, grease, or another substance within the vent 12. In other words, the accumulation sensor 54 is configured to provide feedback indicative of an amount of buildup or accumulation on the interior surface 14 of the vent 12 to the control system 16. For example, FIG. 3 is a schematic of an embodiment of the accumulation sensor 54 monitoring accumulation of a substance 80 deposited along the interior surface 14 of the vent 12. As shown in the illustrated embodiment of FIG. 3, the accumulation sensor 54 may include a photoelectric sensor that includes an emitter 82 and a receiver 84. The emitter 82 is configured to emit a beam of light, such as infrared light, which is shown as line 86. The beam of light 86 reflects off of the interior surface 14 of the vent 12 and/or the substance 80 as reflected light, which is shown as line 88. The reflected light 88 is ultimately detected and received by the receiver 84. As the substance 80 accumulates along the interior surface 14, an intensity of the reflected light 88 may decrease. As such, when the intensity of the reflected light 88 decreases below a threshold level, the control system 16 may determine that the accumulation of the substance 80 has grown to a level that justifies maintenance of the vent 12. In other embodiments, the control system 16 may correlate the intensity of the reflected light 88 to an amount of the substance 80 that has accumulated on the interior surface 14. As such, maintenance of the vent 12 may be appropriate when the amount of the substance 80 exceeds a target or threshold level.

Further, as shown in the illustrated embodiment of FIG. 3, the vent monitoring system 10 includes the temperature sensor 52 configured to provide feedback indicative of a temperature within the vent 12 and/or a temperature of the fluid within the vent 12. In some embodiments, the temperature sensor 52 extends from within the interior 50 of the housing 20 and into the interior portion 22 of the vent 12. As such, the temperature sensor 52 may contact the fluid flowing through the vent 12 to determine a temperature of the fluid. In other embodiments, the temperature sensor 52 may be exposed to the interior portion 22 of the vent 12, but otherwise be flush and/or recessed with an outer surface 90 of the housing 20. In any case, the temperature sensor 52 provides feedback indicative of a temperature in the vent 12 to the control system 16, which may then determine a condition of the vent 12 based on the feedback. For example, when the feedback from the temperature sensor 52 indicates that the temperature within the vent 12 exceeds a threshold amount or value, the control system 16 may determine that the vent 12 is not sufficiently exhausting the fluid, that an excess amount of fuel is being utilized to generate a flame, or that another condition of the vent 12 exists that may warrant maintenance of the vent 12.

Additionally, the vent monitoring system 10 may include the concentration sensor 56 configured to provide feedback indicative of a concentration of a substance, such as a gaseous compound, within the fluid flowing through the vent 12 to the control system 16. Similar to the temperature sensor 52, the concentration sensor 56 may extend from within the interior 50 of the housing 20 and into the interior portion 22 of the vent 12. As such, the concentration sensor 56 may contact the fluid flowing through the vent 12 to determine a concentration of a substance in the fluid, such as carbon monoxide. In other embodiments, the concentration sensor 56 may be exposed to the interior portion 22 of the vent 12, but may otherwise be flush and/or recessed with the outer surface 90 of the housing 20. For example, the vent monitoring system 10 may include a sampling conduit 92 configured to route a portion of the fluid from the interior portion 22 of the vent 12 toward the concentration sensor 56, and from the concentration sensor 56 back to the interior portion 22 of the vent 12. In any case, the concentration sensor 56 provides feedback indicative of an amount of a substance within the fluid. In certain embodiments, the control system 16 may monitor the feedback from the concentration sensor 56 to determine whether an amount of a substance in the fluid exceeds a threshold, or falls below a threshold. For example, the control system 16 may be configured to generate a notification to the external electronic device 32 when an amount of carbon monoxide in the fluid exceeds a threshold amount.

Further still, the vent monitoring system 10 of FIG. 3 includes the flow sensor 58 configured to provide feedback indicative of a flow rate of the fluid through the interior portion 22 of the vent 12. In some embodiments, the flow sensor 58 extends from within the interior 50 of the housing 20 and into the interior portion 22 of the vent 12. As such, the flow sensor 58 may be exposed to or contact the fluid flowing through the vent 12 to determine the flow rate of the fluid. In other embodiments, the flow sensor 58 may be exposed to the interior portion 22 of the vent 12, but may otherwise be flush and/or recessed with the outer surface 90 of the housing 20. For example, the vent monitoring system 10 may include the sampling conduit 92 configured to route a portion of the fluid from the interior portion 22 of the vent 12 toward the flow sensor 58, and from the flow sensor 58 back to the interior portion 22 of the vent 12. In any case, the flow sensor 58 provides feedback indicative of the flow rate of the fluid to the control system 16. In certain embodiments, the control system 16 may generate a notification to be transmitted to the external electronic device 32 when the flow rate of the fluid falls below a threshold amount because the vent 12 may be blocked and/or a condition within the vent, such as a crack or opening, limits the flow of the fluid through the vent 12.

While the above discussion focuses on the control system 16 generating the notification based on an analysis of feedback from individual sensing devices 52, 54, 56, and 58, it should be understood that the control system 16 may cumulatively analyze the feedback from each of the individual sensing devices 52, 54, 56, and 58 to determine a condition of the vent 16. For example, the control system 16 may determine that an accumulation of a substance within the interior portion 22 of the vent 12 is the cause for a reduction in the flow rate of the fluid by comparing the feedback from the accumulation sensor 54 with the feedback from the flow sensor 58. The control system 16 may also determine that a sensing device has experienced an error when feedback from the remaining sensing devices is inconsistent with feedback from the sensing device that has experienced the error. In any event, the control system 16 may aggregate the feedback from each of the sensing devices 52, 54, 56, and 58 to determine a condition of the vent 12 and to output the notification to the external electronic device 32.

Figure 4:
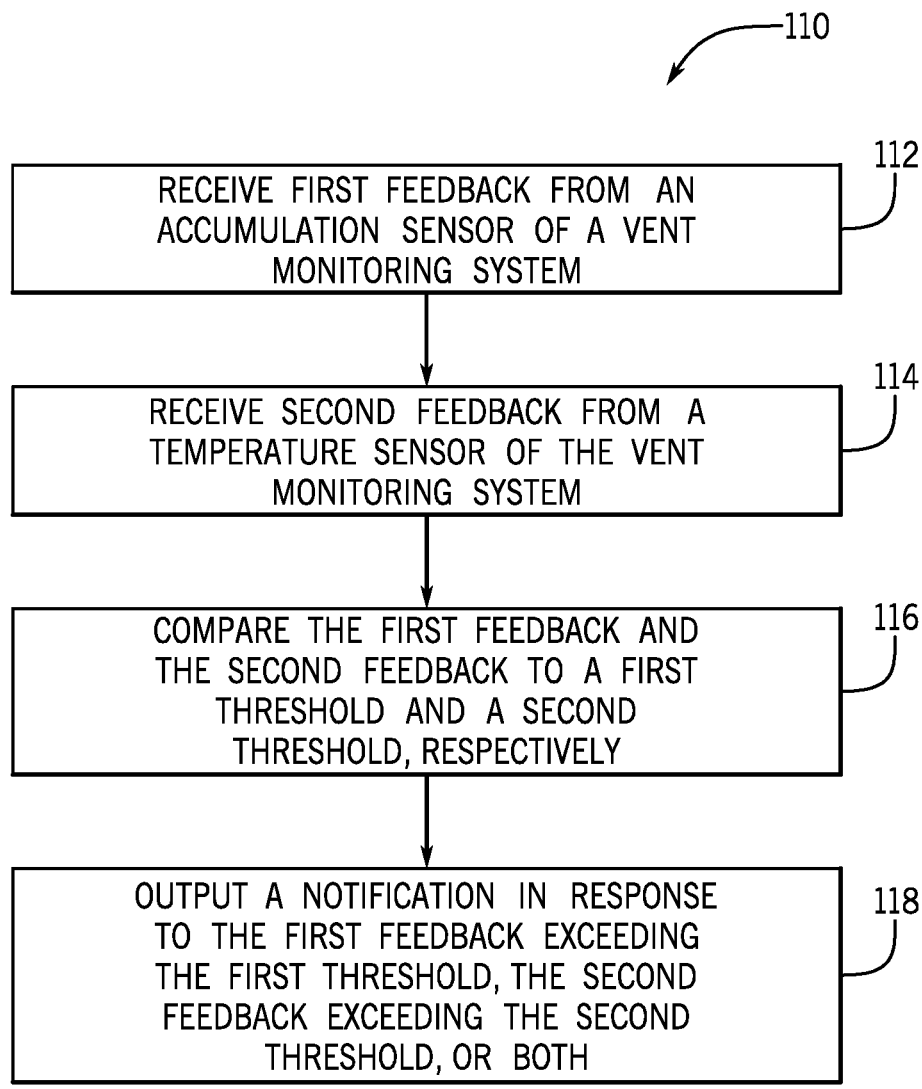
FIG. 4 is a block flow diagram of an embodiment of a process that may be performed by the vent monitoring system of FIGS. 1 and 2, in accordance with an aspect of the present disclosure.

FIG. 4 is a block diagram of an embodiment of a process 110 that may be performed by the vent monitoring system 10 to provide a notification to the external electronic device 32 of the user or serviceperson. For example, at block 112, the control system 16 of the vent monitoring system 10 may receive first feedback from the accumulation sensor 54. As discussed above, the first feedback from the accumulation sensor 54 may be indicative of buildup of a substance along the interior surface 14 based on an intensity of reflected light. Further, at block 114, the control system 16 receives second feedback from the temperature sensor 52. The second feedback from the temperature sensor 52 may be indicative of a temperature within the interior portion 22 of the vent 12 and/or a temperature of the fluid flowing through the vent 12. As discussed above, the control system 16 may also receive feedback from the concentration sensor 56, the flow sensor 58, or another suitable sensor of the vent monitoring system 10.

In any case, at block 116, the control system 16 may compare the first feedback to a first threshold and compare the second feedback to a second threshold. For example, the first threshold may be indicative of an amount of buildup along the interior surface 14 of the vent 12 that reduces an efficiency of the vent 12 by a predetermined percentage. In some embodiments, the first threshold may be an amount, such as an approximate dimension, of buildup that is between 10% and 50%, between 15% and 40%, or between 20% and 30% of a diameter or width of the interior portion 22 of the vent 12. In other embodiments, the first threshold may be indicative of an intensity of the reflected light, such as between 25% and 90%, between 40% and 80%, or between 50% and 75% of the intensity of the light emitted from the emitter 82. The second threshold may be a temperature within the interior portion 22 of the vent 12 that is indicative of a maintenance event, such as cleaning, removing blockage, repairing a burner, or another suitable maintenance event.

At block 118, the control system 16 may generate a notification in response to the first feedback exceeding the first threshold, such as when the first threshold is the threshold amount of buildup in the vent 12. In embodiments where the first threshold is the intensity of the reflected light, the control system 16 may generate a notification in response to the first feedback falling below the first threshold. Additionally or alternatively, the control system 16 may generate the notification in response to the second feedback exceeding the second threshold. As such, the external electronic device 32 may alert the user or serviceperson that the vent 12 should incur maintenance.

As set forth above, embodiments of the present disclosure may provide one or more technical effects useful in monitoring a vent or chimney. For example, embodiments of the present disclosure are directed to a vent monitoring system that includes a plurality of sensing devices configured to monitor conditions within the vent or chimney. The plurality of sensing devices may include a temperature sensor, an accumulation sensor, a concentration sensor, a flow sensor, or another suitable sensor. In any event, a control system of the vent monitoring system may utilize feedback from the plurality of sensing devices to determine whether maintenance to the vent should be performed. When the control system determines that maintenance should be performed, the control system may generate a notification to a user or serviceperson to initiate the maintenance. The technical effects and technical problems in the specification are examples and are not limiting. It should be noted that the embodiments described in the specification may have other technical effects and can solve other technical problems.

While only certain features and embodiments have been illustrated and described, many modifications and changes may occur to those skilled in the art, such as variations in sizes, dimensions, structures, shapes and proportions of the various elements, values of parameters, such as temperatures and pressures, mounting arrangements, use of materials, colors, orientations, and so forth, without materially departing from the novel teachings and advantages of the subject matter recited in the claims. The order or sequence of any process or method steps may be varied or re-sequenced according to alternative embodiments. It is, therefore, to be understood that the appended claims are intended to cover all such modifications and changes as fall within the true spirit of the disclosure. Furthermore, in an effort to provide a concise description of the exemplary embodiments, all features of an actual implementation may not have been described, such as those unrelated to the presently contemplated best mode, or those unrelated to enablement. It should be appreciated that in the development of any such actual implementation, as in any engineering or design project, numerous implementation specific decisions may be made. Such a development effort might be complex and time consuming, but would nevertheless be a routine undertaking of design, fabrication, and manufacture for those of ordinary skill having the benefit of this disclosure, without undue experimentation.

The invention claimed is:

1. A monitoring system for a vent, comprising:
    a first sensor configured to detect a substance accumulated on an interior surface of the vent and provide feedback indicative of an amount of the substance accumulated on the interior surface of the vent, wherein the first sensor is exposed to the interior surface;
    a second sensor configured to provide feedback indicative of a temperature in the vent; and
    a control system communicatively coupled to the first sensor and the second sensor, wherein the control system is configured to generate a notification when the feedback from the first sensor exceeds a first target level and when the feedback from the second sensor exceeds a second target level,
    wherein the vent defines an interior configured to receive and direct a fluid along a flow path extending through the interior of the vent, the first and second sensors are mounted to the interior surface of the vent within the interior of the vent, and at least one of the sensors is in contact with the fluid.

2. The monitoring system of claim 1, wherein the first sensor comprises a photoelectric sensor.

3. The monitoring system of claim 2, wherein the photoelectric sensor comprises an emitter and a receiver.

4. The monitoring system of claim 3, wherein the emitter is configured to emit a beam of light toward the interior surface of the vent, and wherein the receiver is configured to receive a reflected beam of light reflected from the interior surface of the vent, the substance accumulated in the vent, or both.

5. The monitoring system of claim 4, wherein the feedback from the first sensor is indicative of an intensity of the reflected beam of light, the substance accumulated in the vent, or both, and is received by the receiver.

6. The monitoring system of claim 5, wherein the control system is configured to correlate the feedback from the first sensor with the amount of the substance accumulated on the interior surface of the vent.

7. The monitoring system of claim 1, wherein the first sensor is configured to provide feedback indicative of an amount of creosote, grease, ash, dust, lent, or a combination thereof, accumulated in the vent.

8. The monitoring system of claim 1, comprising:
    a third sensor configured to provide feedback indicative of an amount of a gas within a fluid in the vent; and
    a fourth sensor configured to provide feedback indicative of a flow rate of the fluid through the vent;
    wherein the third sensor and the fourth sensor are communicatively coupled to the control system, and the control system is configured to generate the notification when the feedback from the third sensor exceeds a third target level, when the feedback from the fourth sensor exceeds a fourth target level, or both.

9. The monitoring system of claim 8, wherein the gas comprises carbon monoxide.

10. The monitoring system of claim 8, wherein the control system is configured to generate the notification via a cumulative analysis of the feedback from the first sensor, the feedback from the second sensor, the feedback from the third sensor, and the feedback from the fourth sensor.

11. The monitoring system of claim 1, wherein the control system is configured to transmit the notification to an external electronic device.

12. The monitoring system of claim 11, wherein the control system is configured to be communicatively coupled to the external electronic device via Wi-Fi, Bluetooth, Zigbee, or another wireless communication protocol.

13. The monitoring system of claim 11, wherein the notification to the external electronic device comprises a text message, a phone call, an e-mail, a push notification, an audible alert, or any combination thereof.

14. The monitoring system of claim 1, wherein the vent comprises a chimney.

15. A monitoring system, comprising:
    a housing configured to be mounted to an interior surface of a vent;
    a first sensor disposed at least partially within the housing, wherein the first sensor is configured to detect a substance accumulated in the vent and provide feedback indicative of an amount of the substance accumulated in the vent;
    a second sensor disposed at least partially within the housing, wherein the second sensor is configured to provide feedback indicative of a temperature in the vent; and
    a control system disposed within the housing, wherein the control system is communicatively coupled to the first sensor and the second sensor, and the control system is configured to generate a notification to perform maintenance on the vent when the feedback from the first sensor reaches a first target level, when the feedback from the second sensor reaches a second target level, or both,
    wherein the vent defines an interior configured to receive and direct a fluid along a flow path extending through the interior of the vent, the housing, including the first and second sensors, mounted within the interior of the vent.

16. The monitoring system of claim 15, wherein the second sensor is configured to extend from an interior of the housing and into the interior of the vent.

17. The monitoring system of claim 15, wherein the first sensor comprises a photoelectric sensor.

18. The monitoring system of claim 17, wherein the photoelectric sensor is disposed completely within the housing.

19. The monitoring system of claim 15, comprising:
a third sensor disposed at least partially within the housing, wherein the third sensor is configured to provide feedback indicative of an amount of a gas within a fluid in the vent; and
a fourth sensor disposed at least partially within the housing, wherein the fourth sensor is configured to provide feedback indicative of a flow rate of the fluid;
wherein the third sensor and the fourth sensor are communicatively coupled to the control system, and the control system is configured to generate the notification to perform maintenance on the vent when the feedback from the third sensor reaches a third target level, when the feedback from the fourth sensor reaches a fourth target level, or both.

20. The monitoring system of claim 19, wherein the control system is configured to generate the notification to perform maintenance on the vent via a cumulative analysis of the feedback from the first sensor, the feedback from the second sensor, the feedback from the third sensor, and the feedback from the fourth sensor.

21. A tangible, non-transitory, machine-readable medium, comprising instructions that, when executed by a processor, cause the processor to:
receive feedback from a first sensor of a vent monitoring system, wherein the feedback from the first sensor is indicative of a detected amount of a substance accumulated on an interior surface of a vent;
receive feedback from a second sensor of the vent monitoring system, wherein the feedback from the second sensor is indicative of a temperature within the vent;
compare the feedback from the first sensor to a first threshold value and compare the feedback from the second sensor to a second threshold value; and
output a notification to perform maintenance on the vent in response to the feedback from the first sensor exceeding the first threshold value, the feedback from the second sensor exceeding the second threshold value, or both,
wherein the vent defines an interior configured to receive and direct a fluid along a flow path extending through the interior of the vent, and the first and second sensors are mounted to the interior surface of the vent within the interior of the vent.

22. The tangible, non-transitory, machine-readable medium of claim 21, wherein the instructions, when executed by a processor, cause the processor to:
receive feedback from a third sensor of the vent monitoring system, wherein the feedback from the third sensor is indicative of an amount of a gas within the fluid in the vent;
compare the feedback from the third sensor to a third threshold value; and
output the notification in response to the feedback from the third sensor exceeding the third threshold value.

23. The tangible, non-transitory, machine-readable medium of claim 22, wherein the instructions, when executed by a processor, cause the processor to:
receive feedback from a fourth sensor of the vent monitoring system, wherein the feedback from the fourth sensor is indicative of a flow rate of the fluid in the vent;
compare the feedback from the fourth sensor to a fourth threshold value; and
output the notification in response to the feedback from the fourth sensor exceeding the fourth threshold value.

24. The tangible, non-transitory, machine-readable medium of claim 23, wherein the instructions, when executed by a processor, cause the processor to output the notification based on a cumulative analysis of the feedback from the first sensor, the feedback from the second sensor, the feedback from the third sensor, and the feedback from the fourth sensor.

* * * * *